US008229672B2

(12) United States Patent
Prigge et al.

(10) Patent No.: US 8,229,672 B2
(45) Date of Patent: Jul. 24, 2012

(54) PERCOLATION TEST APPARATUS

(76) Inventors: Brian Lee Prigge, St. Cloud, MN (US); Chad Michael Kraemer, Cold Spring, MN (US)

( * ) Notice: Subject to any disclaimer, the term of this patent is extended or adjusted under 35 U.S.C. 154(b) by 307 days.

(21) Appl. No.: 12/566,375

(22) Filed: Sep. 24, 2009

(65) Prior Publication Data

US 2010/0082259 A1 Apr. 1, 2010

Related U.S. Application Data

(60) Provisional application No. 61/099,825, filed on Sep. 24, 2008.

(51) Int. Cl.
*G06F 19/00* (2006.01)
(52) U.S. Cl. ........................................................ 702/12
(58) Field of Classification Search .................... 702/12, 702/13, 14, 182–185, 188
See application file for complete search history.

(56) References Cited

U.S. PATENT DOCUMENTS

| | | |
|---|---|---|
| 3,926,143 A | 12/1975 | Hothan |
| 4,099,406 A | 7/1978 | Fulkerson |
| 4,182,157 A | 1/1980 | Fink |
| 4,341,110 A | 7/1982 | Block |
| 4,561,290 A | 12/1985 | Jewell |
| 4,829,817 A | 5/1989 | Kozlowski |
| 4,984,447 A | 1/1991 | Phillips |
| 6,055,850 A | 5/2000 | Turner et al. |
| 6,105,418 A | 8/2000 | Kring |
| 6,274,033 B1 | 8/2001 | Hudgin |
| 7,062,957 B2 | 6/2006 | Power |
| 2006/0277980 A1* | 12/2006 | Kristiansen ..................... 73/73 |

FOREIGN PATENT DOCUMENTS

| | | |
|---|---|---|
| JP | 61191712 | 8/1986 |
| WO | WO-03/054307 | 7/2003 |

OTHER PUBLICATIONS

PCT International Search Report and Written Opinion from International Application No. PCT/IE02/00172, corresponding to U.S. Patent 7,062,957, mailed Jul. 3, 2003, pp. 1-2.
Gustafson, David et al., "How to Run a Percolation Test", *University of Minnesota—Onsite Sewage Treatment Program* pp. 1-9.
Lentz, Rodrick D., "Automated System for Collecting Multiple, Sequential Samples from Soil Water Percolation Samplers under Continuous Vacuum", Communications in Soil Science and Plant Analysis 2006 , vol. 37, Issue 9 & 10, pp. 1195-1203.

* cited by examiner

*Primary Examiner* — Edward Raymond
(74) *Attorney, Agent, or Firm* — Pauly, Devries, Smith & Deffner, L.L.C.

(57) ABSTRACT

The present invention includes a method and apparatus for determining the percolation rate of soil. The method includes providing a test assembly configured to be placed over the top of a test hole, the test assembly containing a remote sensor (such as an ultrasound sensor) positioned proximate the top of the hole. The depth to the bottom of the hole, as well as the elevation of water within the hole during the test process, is measured using the remote sensor and used to determine perc rate of the soil within which the hole is dug.

22 Claims, 5 Drawing Sheets

PERCOLATION TEST APPARATUS

This application claims the benefit of U.S. Provisional Application No. 61/099,825 filed Sep. 24, 2008, the contents of which are herein incorporated by reference.

FIELD OF THE INVENTION

The present invention is directed to percolation testing equipment and methods for use in soil testing.

BACKGROUND OF THE INVENTION

Adequate treatment and disposal of human waste is essential to preserve public health. Failure to properly treat and dispose of human waste results in a heightened risk of disease outbreaks, such as from cholera and bacterial agents. In addition, improper waste disposal often results in environmental degradation as water sources are loaded with excess nutrients. This excess nutrient loading can result in elevated nitrate levels in aquifers, unattractive algae blooms in lakes and rivers, and anoxic conditions developing in surface waters as algae blooms die and decay.

In modern urban areas sewer and water treatment occurs at centralized sewer treatment facilities equipped to properly handle large levels of waste. In rural areas not serviced by sewer systems, a method of disposal of common household and human wastes is necessary. For these rural areas an anaerobic treatment process known as a septic system is often employed. In most septic systems the treatment process consists of a series of typical steps: a septic tank collects the wastes from the house, biological processes occur in the septic tank that result in converting solids to liquids, an absorption field is dosed with effluent from the septic tank that is deposited into the soil from pipes with holes, and finally the absorption field soil converts the waste water to clean water.

Locating and designing a septic system in an area with suitable soil is critical to providing adequate on site sewage treatment. Soil that is too coarse will not adequately remove nutrients and bacteria. Loam or clay loam soils can do an excellent job of nutrient and bacteria removal but require a relatively large soil treatment area.

Therefore, the soil absorption rate is a critical element of proper septic placement, sizing, and construction. If the absorption rate is too slow it will cause the sewage to back up into the house or move over the surface of the soil. If the absorption rate is too fast, it will allow insufficient time for microbes in the soil to clean the water. Also, if space is limited or soil conditions are poor, homeowners may need a modified treatment system.

In order to measure soil absorption, a percolation test is performed to calculate perc rate by measuring the time it takes water to drop a predetermined amount in a pre-wetted hole, typically time divided by drop in water level, often expressed as minutes per inch of water level drop. However, existing equipment for measuring the perc rate is inadequate in numerous regards: it is cumbersome to use, can be imprecise, and is very time consuming to properly operate. Typical equipment in use today involves, for example, manual operation of floats, measuring sticks and a timing device to determine perc rate. Typically, a technician must stay with the rudimentary test equipment to collect and analyze readings for a multi-hour period.

Modifications have been made in some percolation test equipment, such as that disclosed in U.S. Pat. No. 7,062,957 to inventor Martin Power. One of the problems with the Power design is that it is cumbersome, typically requiring creation of a large hole for the perc testing equipment (necessitating large amounts of water for the perc test and a greater impact on test area from the larger hole or holes) and lowering of a screen into the hole to stabilize the opening. The large hole can be dug, for example, using a truck-mounted backhoe that is heavy, hard to maneuver in small spaces, and expensive. Also, the Power method lowers a sensor into a hole to measure the level of water in the hole. Clearly the Power method has significant limitations, due to the overall design and the manner in which level measurements are made.

Therefore, a need exists for improved perc test equipment that allows fast, accurate, efficient perc testing.

SUMMARY OF THE INVENTION

The present invention is directed to a new soil percolation apparatus and method that allows very fast, accurate, and efficient perc testing of soils. The apparatus and method rely upon a design that does not place measuring instruments into the soil bore hole, thereby simplifying the measurement process while allowing a more accurate and precise measurement to be made. Notably, the present method and system allow for sophisticated control of water flow and measurement, as well as precise recordation of test locations. In addition, the present invention is advantageous because it allows for a compact, portable unit that can be readily installed in remote field locations, and that after installation it runs substantially independently with little or no intervention from the start of the test to completion of the test.

In certain embodiments of the invention the sensing of water levels is measured by a top-mounted sensor that is directed down into the test bore hole. The sensor is configured to measure the depth of the hole without the need to place any measuring device down into the hole. In this regard, the sensor is referred to herein as a "remote sensor" because the level of water is measured without contacting the water. It will be understood that a "remote sensor" can include an ultrasonic sensor, but is not limited to ultrasonic sensors. An ultrasonic sensor is particularly useful because it can be used to measure with great precision changes in water levels in the test bore hole as water is initially added to the bore hole to soak the hole, as well as to measure the flow of water out of the bore hole as the perc test continues. However, other sensors besides ultrasonic sensors can be used in certain implementations of the invention. For example, optical sensing technology (such as infrared and laser), radio frequency sensing, or other remote sensing technologies can all be used with the current invention. In this regard, various embodiments are described in terms of use with an ultrasonic sensor. However, it will be appreciated that other remote sensing methods can be used and are expressly covered by the application.

Automation of the perc test process allows for the entire percolation test to be undertaken without further intervention after the test has been set up. This allows a significant savings in labor over prior methods. For example, it is possible to have the perc test run substantially independently after the equipment has set up, and to even have the results printed on-site and/or electronically sent to an external receiving location (such as a networked database for recording test results).

In one aspect of the invention, a method of determining the percolation rate of soil is described. As a first step, a hole must be dug into the soil area to be tested. Thereafter a test assembly made in accordance with the invention is placed over the top of the hole, the test assembly containing a remote sensor (such as an ultrasonic sensor or other remote sensor) positioned at the top of the hole and directed down into the hole.

It is not necessary to have any other probe or measuring device reach down into the hole. The depth to the bottom of the hole is then typically measured, and the hole is automatically filled with an amount of water sufficient to reach a desired water level in the hole, generally around twelve inches in most embodiments, although greater and lesser levels can be used in some examples.

In certain aspects of the invention, the method includes a further step of making an initial determination as to whether the hole is retaining water at a rate sufficient to conduct a "short" test or a "long" test. If the borehole is shown to be losing water rapidly when it is first filled, then a "short" test can be conducted wherein the hole is filled a set amount, and immediately thereafter the rate at which the water level decreases per time period is measured. In contrast, when a "long" test is run, typically the level of water in the hole is maintained for an extended period of time to soak the soil test area, and thereafter the test area may be allowed to "swell" for an extended period of time before refilling the hole for the actual measurements of water level decreases over time. Thus, the major difference between the short and long tests are that the short test does not involve a soak or swell period.

With regard to the long test, it is often it is necessary to maintain a twelve inch level of water for an extended period (of four or more hours for example) to soak the soil in the test area. In some cases local or state rules will have a specific time period during which levels adequate to soak the hole must be maintained. During this time of soaking the hole, the remote sensor continually monitors the level of water in the hole, maintains the level of water as it is absorbed into the soil test area. For example, it is possible to have the apparatus programmed such that water is added every time the water level in the hole drops below 11 inches, and the water is added in sufficient volume to fill the hole back up to 12 inches or optionally higher. It will be appreciated that other levels are also possible in certain embodiments, often depending upon local and state regulations as to how long and how deep the "soaking" period should occur. In some tests a "swell" period (of 16 to 30 hours for example) is also required after the soaking period. During the swell period the hole remains empty. The apparatus of the present invention typically starts measuring the swell period after the hole is determined to be empty or substantially empty.

For example, in a typical implementation, the hole depth will first be measured by the apparatus of the invention, then water will be added to the hole in a volume sufficient to raise the water level to twelve inches, followed by a soaking period (of 4 hours, for example) during which water is periodically added to the hole to maintain the water level in response to measurements made by the remote sensor. After the 4 hour soaking period, the hole is allowed to drain completely, beginning a new measured swell period (of 16 to 30 hours, for example).

After an adequate soaking/swell period the timed drop in water level is measured to determine the perc rate of the soil. Percolation rate is calculated by allowing water to slowly soak out of the bore hole, measuring the time and distance dropped. The time interval is divided by the drop in water level to determine the percolation rate in minutes per inch (MPI). For example, if the drop in water level is one inch in 30 minutes, the percolation rate is 30 minutes/1 inch=30 mpi. If the drop is 2½ inches in 10 minutes, then the percolation rate is 10 minutes/2.5 inches=4 mpi.

When three consecutive measured percolation rates of the apparatus vary by no more than 10 percent, the average value of these readings is used to determine the percolation rate for the test hole. Often it is desirable to measure the percolation rate at two or more holes to identify the slowest percolation rate, which is then used for designing the septic system.

A further useful implementation comprises recording the location of the remote sensor using a global positioning system (GPS) receiver to record the precise location of the perc test. The GPS receiver can be used to interface with other features of the invention (notably a printer, described below). Typically the GPS receiver is integrated directly into the apparatus of the invention, allowing it to communicate with other components of the test apparatus. The GPS receiver can also be used to reduce the risk of fraudulent tests being conducted by recording the location of the test.

The apparatus of the present invention typically includes a printer used to produce a printed result showing perc at the test location. One advantage of using a printer that is integral to the test assembly is that precise test results can be recorded without the introduction of errors. Thus, labor is reduced along with an increase in accuracy. It will be appreciated that the printer can optionally output just minimal information, such as date, and perc test results; or can output more detailed information, including the time each step occurred (such as depth of the hole, when the hole was filled, when the hole was allowed to soak, when it was allowed to swell, and multiple readings for level and time, machine serial number, etc.). Also, as described above, data such as location can be generated by GPS so as to make location recordation more accurate, less prone to error, and less prone to fraudulent results.

A major advantage of the present invention, which typically uses just one remote sensor to measure multiple levels, is that not just the level of water but also the depth to the bottom of the hole is measured by the remote sensor. Thus, the remote sensor can provide multiple functions by both assessing the nature of the hole (its depth) as well as the level of water within the hole. This allows ease of use, as well as great accuracy in the test results because the depth of the hole is precisely known. Also, changes in hole depth, such as collapsing of the hole, can be measured and accounted for using the present invention because hole depth will have changed during the testing (such as a shallower hole depth measured after the swell period compared to the initial depth, as a result of a collapse of the side of the hole, resulting in debris collecting at the bottom of the hole. Thus, the method of the present invention also includes the ability to measure and report whether a bore hole has collapsed. This is possible by measuring the depth of the hole at the start of the test and the end of the test using the remote sensor of the invention. If the hole has collapsed, then the collapse will be apparent by observing a meaningful decrease in the depth of the hole from the start of the test to the end of the test. Such collapses can be informative because they change the surface area of the hole, thereby potentially providing an inaccurate perc test measurement.

In certain implementations the invention can include a mode that determines the depth of the hole by adding water. This is useful, for example, when an initial reading from the remote sensor does not produce an accurate indication of hole depth. This is possible, for example, when the hole has an uneven bottom. In such implementations a small amount of water is added to the hole until a reading is obtained by the remote sensor. In the case of ultrasonic sensors, the water in the hole creates a planar surface that reflects the sound waves well, thereby allowing the hole depth to be measured.

In some implementations, multiple percolation test assemblies can be connected to conduct multiple tests simultaneously. In some such embodiments one base optionally station controls one or more remote devices. Typically the multitude of percolation test assemblies utilize a common water supply. Also, in most implementations there will be one primary test assembly that controls one or more (often two) other test assemblies. In this manner, key features such as GPS receiver, wireless transmitters, printers and some control and processing equipment does not need to be duplicated in every test assembly. In some implementations it is most useful to have the primary assembly contain the GPS receiver, wireless transmitters, printers, it's own remote sensor and water control means, and main processor, while secondary assemblies contain a remote sensor and water control means (such as a solenoid-controlled valve).

In yet another aspect, the invention includes a percolation test apparatus comprising a housing; a processor at least partially contained in the housing; a remote sensor configured to determine the depth of a hole and the water level in it and electronically communicate with the processor; a conduit configured to receive water from a water source and allow passage of water into the hole; and a valve in communication with the processor configured to allow and inhibit water flow through the conduit.

In some implementations, the invention further includes functionality allowing wireless communications with an external network or base station. For example, percolation test results can be communicated wirelessly back to a network for processing, archiving, forwarding on to regulatory agencies, etc. Also, optionally, the wireless system can report if the unit is stolen, and can communicate (such as by text message), with external systems to report it has been stolen, as well as its current location. In some implementations the wireless communications equipment will allow for communication between the test equipment and a local area network, such as a WiFi receiver or a portable computer equipped with Bluetooth (or similar method of), functionality. In this implementation, the test equipment will be able to input the test results to the test report form automatically, increasing efficiency and reducing the opportunity for error. In other implementations, the wireless communications equipment will allow for wide area network communication, such as over a cellular network. Notably in some implementations control of the test equipment will be undertaken over the wireless connection, such as updates to the instrument database, system parameter settings, etc. This feature can also be very useful, for example, to enable a field technician using a portable computer to program the test equipment or add important information (again, such as address of the test) using the portable computer.

Another optional feature is the ability to measure for unexpected water source additions. Using the remote sensor of the invention, it is possible to identify whether water is added from an outside source (such as a hose or rain runoff). This can identify faulty test results, whether intentional or accidental, thereby helping to assure the test results are accurate.

The above summary of the present invention is not intended to describe each discussed embodiment of the present invention. This is the purpose of the figures and the detailed description that follows.

BRIEF DESCRIPTION OF THE DRAWINGS

The technology will now be described in greater detail, by way of example, with references to the drawings, in which.

Figure 1:
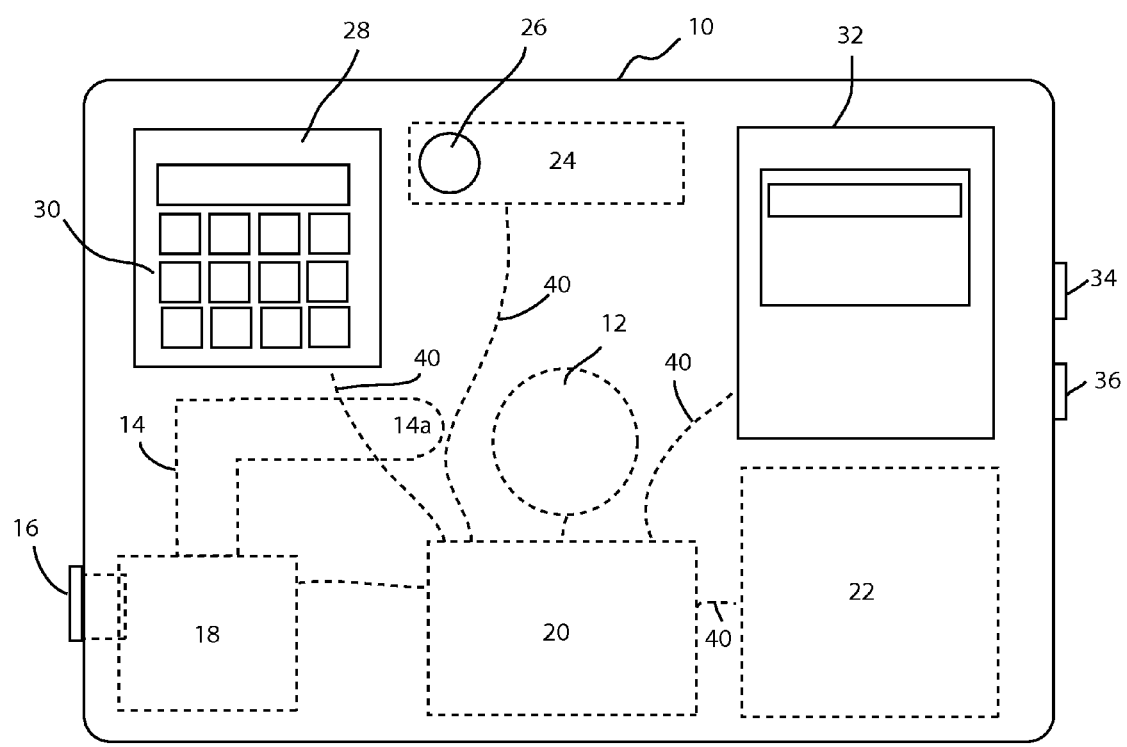
FIG. 1 is a top plan view of an example perc test apparatus made in accordance with the present invention.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

The present invention is directed to a new, compact, portable, soil percolation testing apparatus and method that allows very fast, accurate, and efficient perc testing of soils. The apparatus, in certain embodiments, comprises a substantially self contained measuring and processing unit that allows ease in transport; rapid setup, precise measurement, and ease in reporting. The apparatus and method rely upon a design that does not require the placement of measuring instruments into the soil bore hole, but instead makes measures from the top of the hole. In this way, the apparatus and method simplify the measurement process while allowing a more accurate and precise measurement to be made. Notably, the present method and system allow for sophisticated control of water flow and measurement, as well as precise recordation of test locations.

In certain embodiments of the invention the sensing of water levels is measured by a top-mounted ultrasonic sensor that is directed down into the test bore hole. The ultrasonic sensor is configured to measure the depth of the hole without the need to place any further measuring device down into the hole. In addition, the ultrasonic sensor is particularly useful because it can be used to measure with great precision changes in water levels in the test bore hole as water is added to the hole. The ultrasonic sensor is also well suited to measure the decrease in level as the water in the hole absorbs into the soil as the perc test continues. Automation of the process allows for the entire percolation test to be undertaken without further intervention after the test has been set up. This allows a significant savings in labor over prior methods. As noted earlier, it will be appreciated that other remote sensors can be used in addition to, or instead of, an ultrasonic probe. For example, an infrared or laser ranging system can be used.

Referring now to the drawings, FIG. 1 is a top plan view of an example measuring apparatus made in accordance with the present invention. Items in dashed lines are typically beneath a cover, while items in solid lines are typically exposed on top of the cover (although a lid is still also used to protect the exposed items). As indicated, the apparatus 10 can include a depth measuring remote sensor 12, often an ultrasonic sensor, which is directed downward from the apparatus 10. The depth measuring remote sensor 12 is here shown in dashed lines, since it is generally not visible from the top of the apparatus 10, but is exposed at the bottom of the apparatus 10. Generally a cap or other protective cover can be placed over exposed portion of the remote sensor, but the cap is removed during the test itself The cap protects the remote sensor during transport and storage. Also, it will be appreciated that it is often desirable to have the remote sensor recessed within the case of the apparatus 10, so that the remote sensor is less likely to be damaged during transport or handling.

In addition, it will be observed that central controller 20 is connected to the remote sensor 12, and also connected by means of wires 40 to a solenoid 18, an optional GPS unit 24, an optional printer 32, and a battery 22. The battery provides power to the apparatus 10, and any other neighboring test apparatus that are used. In the alternative, other power supplies may be used. The solenoid 18 is connected to an inlet 16 and an outlet line 14 terminating in outlet 14a. The inlet receives water from a source, such as a barrel or other source, and the outlet 14a is placed over a borehole to deliver water into the hole. Notably, outlet 14a can also be placed on the underside of the apparatus 10 in closer proximity to the remote sensor 12 so that both the outlet 14a and remote sensor 12 apparatus are located in direct proximity to the borehole with the remote sensor centered over the hole. GPS unit 24 includes (in the depicted embodiment) an antenna 26. Also shown is a control interface 28 with buttons 30, a printer 32 for printing perc test results, and two optional connectors 34, 36 for joining the apparatus 10 with other test units for simultaneous perc testing.

It will be appreciated that the test result data will be stored in the controller 20. One of the significant advantages of the present invention is that it allows, in certain implementations, for printer 32 to be integrated into the apparatus 10 to provide test results that are both immediate and verifiable. Thus, printer 32 can be used to print out the perc test results immediately after the test has been performed, and/or the test results can be stored in memory printed at a later time. In some implementations, the GPS unit 24 can be used to supply location information to the controller to be included in the test results, stored and displayed, and or printed. The printing of the location of the test right on the print results helps eliminate potential errors, as well as making fraudulent test more difficult.

It will be appreciated that the function of these various components can be separated or combined in implementations of the invention. For example, the central controller and operator interface can be combined into one unit. Printers, GPS receivers, wireless transmitters, and other components can also be combined together and/or with other components such as the central controller. Therefore, the configurations shown here are only examples, and alternatives that combine or divide functionality between components are deemed to be within the scope of the invention.

Figure 2:
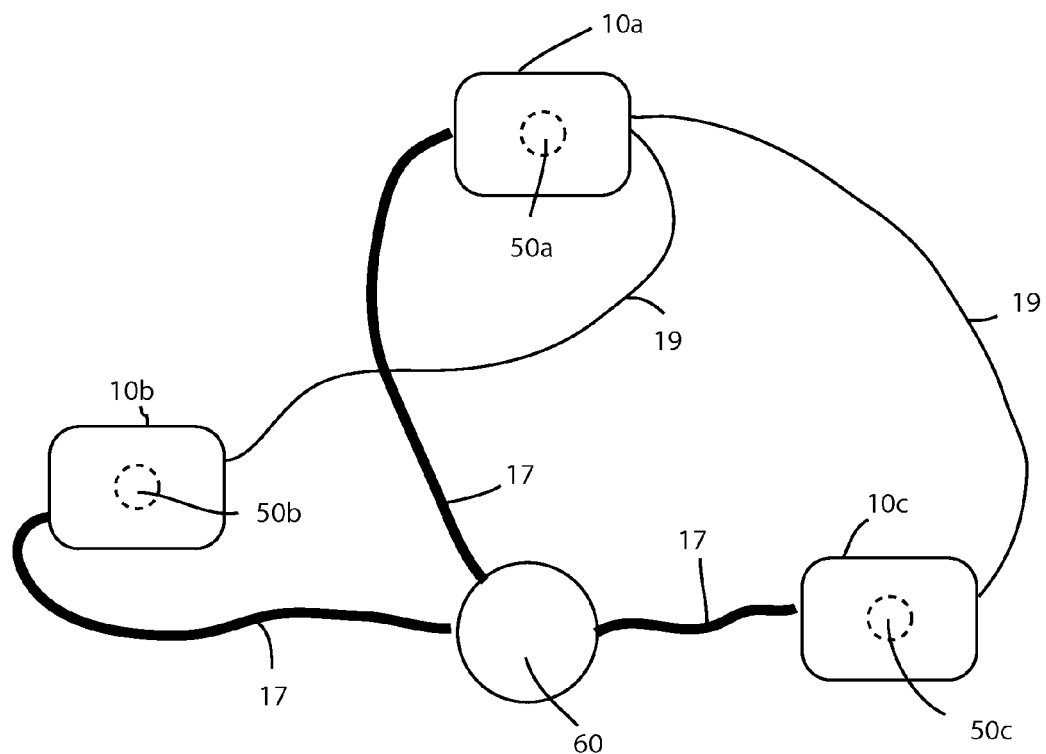
FIG. 2 is a top plan view of a plurality of perc test apparatuses installed in the field for measuring soil perc.

FIG. 2 is a top plan view of a plurality of perc test apparatuses installed in the field for measuring the soil absorption rates, for undertaking simultaneous perc tests. Here, an apparatus 10a is connected to secondary units 10b and 10c by way of control wires 19. A dashed line shows the bore holes 50a, 50b, and 50c to show positioning of the test apparatuses over the top of the bore holes 50a, 50b, and 50c. Also shown is a series of hoses 17 connecting to water source 60 (optionally connected to a faucet, for example).

Figure 3:
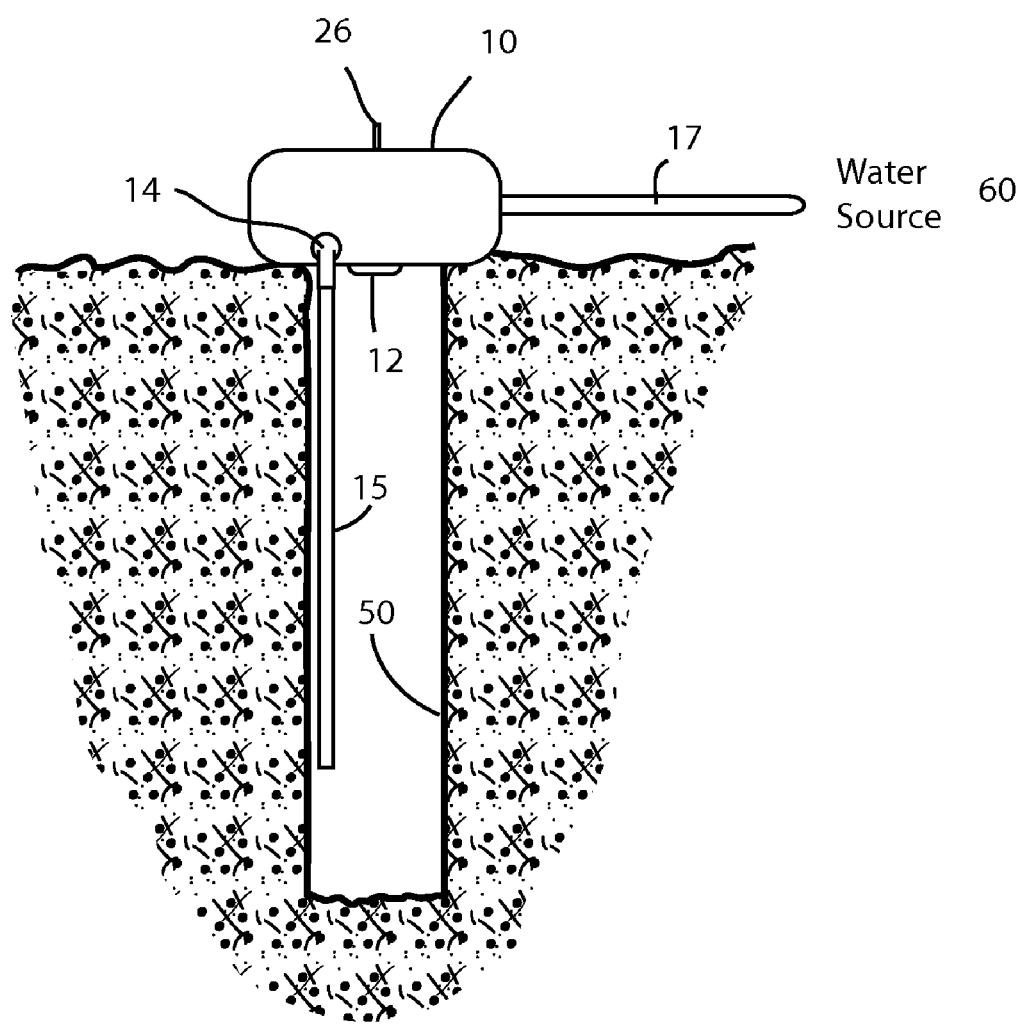
FIG. 3 is a side plan view of an apparatus made in accordance with an implementation of the invention, the perc test apparatus installed over a hole dug into an area to be tested.

FIG. 3 is a side plan view of an apparatus made in accordance with an implementation of the invention, the perc test apparatus installed over a hole dug into an area to be tested. As can be seen, bore hole 50 is dug into the ground to be tested, and apparatus 10 is placed over the top of the bore hole, with remote sensor 12 and water outlet 14 over the opening of the bore hole 50. Water outlet 14 in the depicted embodiment includes a dispensing hose 15 extending from the outlet 14 to near the bottom of the bore hole 50. The dispensing hose 15 is typically removable from the outlet 14. It will be understood that in some implementations the outlet 14 is at the bottom of the apparatus 10 (as opposed to the side as shown in FIG. 3). The dispensing hose 15 is advantageous because it minimizes splashing at the bottom of the bore hole 50, thereby avoiding undesirable erosion in the borehole. It is possible to use dispensing hoses 15 of various lengths. In some implementations the dispensing hose 15 is of a fixed length, while in other implementations the dispensing hose 15 is variable in length—such as by having separable segments that screw together or by having a collapsible hose that is made shorter and longer in an accordion style. Also it is possible to use a fixed length hose or multiple hoses for different depth holes. Generally the dispensing hose 15 is flexible, and typically removable from the outlet 14 of the apparatus 10 for storage or transport. The dispensing hose 15 typically extends at least down at least 50 percent of the depth of the bore hole 50, more often at least 75 percent of the depth of the bore hole 50. Typical dispensing hoses are greater than 2 feet in length, often greater than 3 feet, optionally greater than 4 feet.

Water source 60 is shown, along with hose 17 connecting the water source 60 to the test apparatus 10. Further depicted is a GPS antenna 26 in the depicted embodiment (note that the GPS unit is optional, and in certain embodiments an internal GPS antenna is used so that no external antenna is visible).

Figure 4:
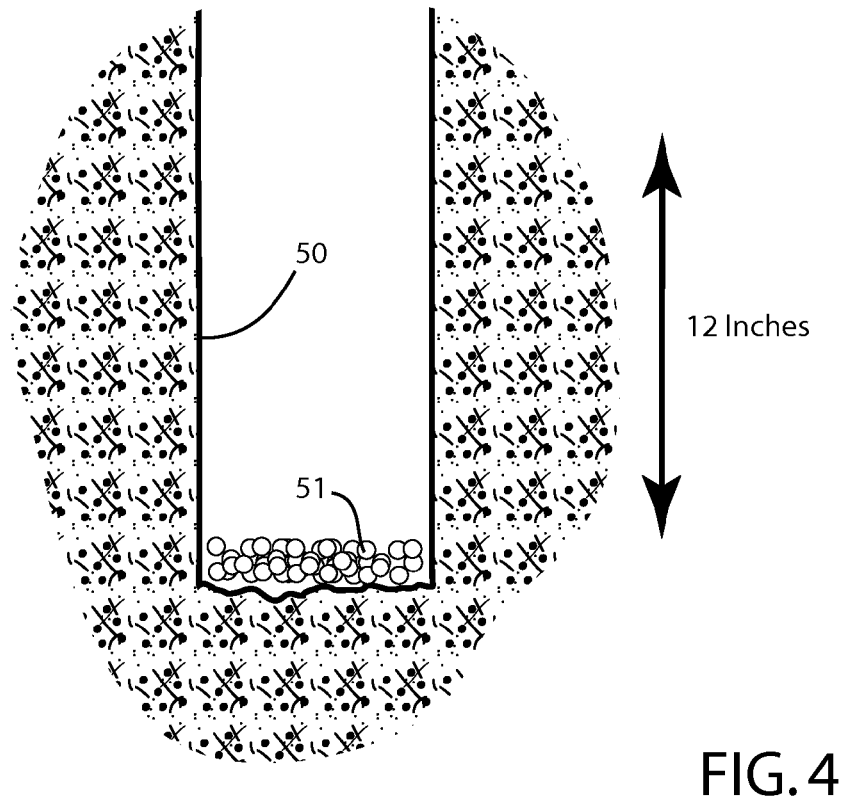
FIG. 4 is a side plan view of test hole prior to addition of water.

FIG. 4 is a close-up of a side plan view of test hole prior to addition of water. Here, gravel 51 has been added to the bottom of the hole.

Figure 5:
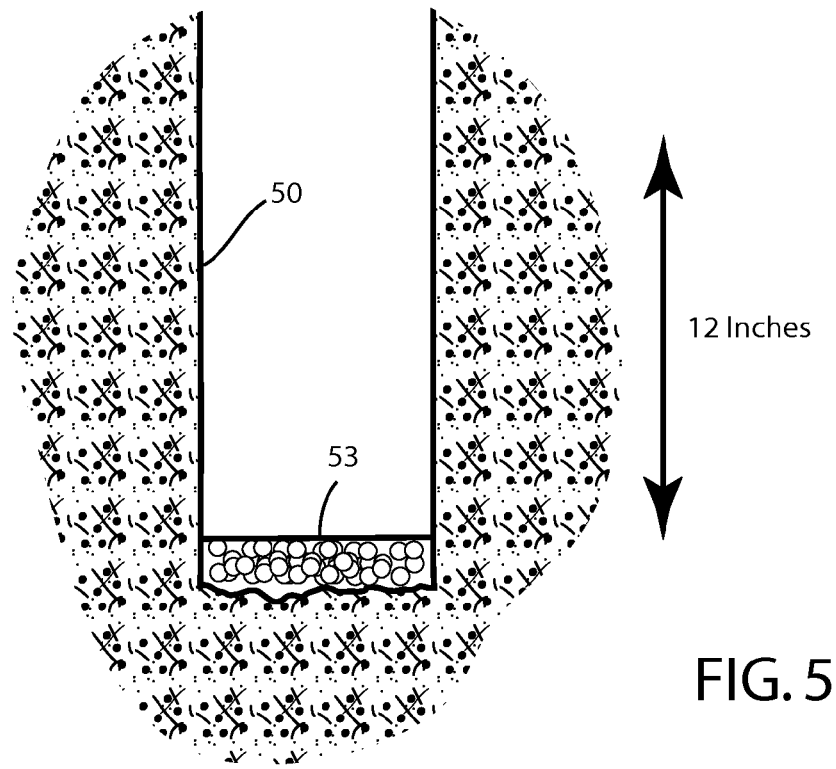
FIG. 5 is a side plan view of test hole after initial addition of water.

FIG. 5 is a close-up of a side plan view of test hole after initial addition of water, such as to register the depth of the hole 50. The elevation of the water is shown as line 53.

Figure 6:
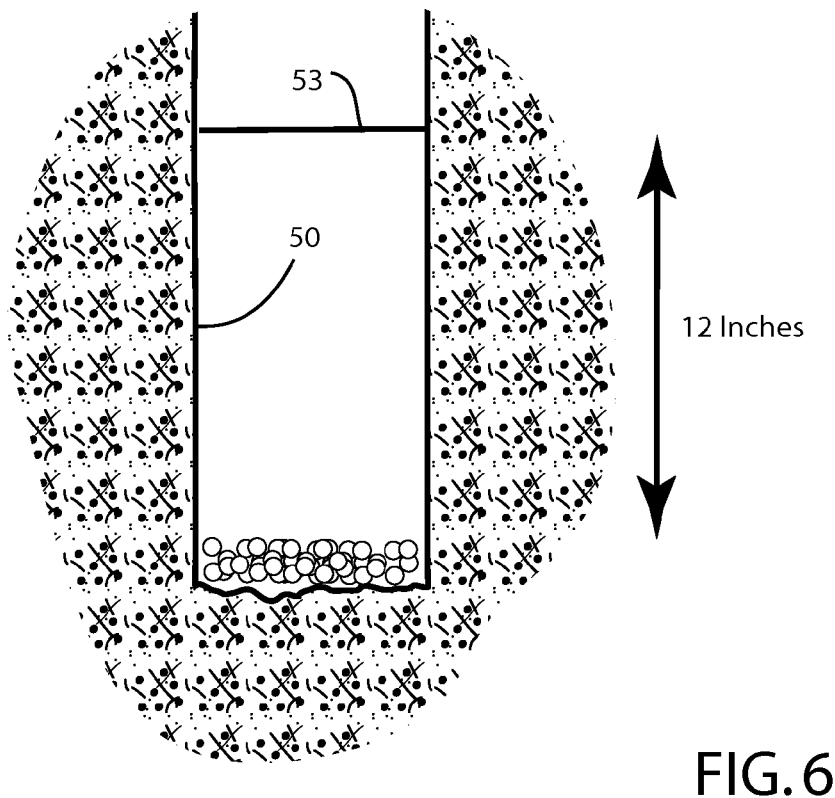
FIG. 6 is a side plan view of test hole during soaking of the test hole.

FIG. 6 is a close-up of a side plan view of test hole during soaking of the test hole, with water level 53 approximately 12 inches above the bottom of the hole.

Figure 7:
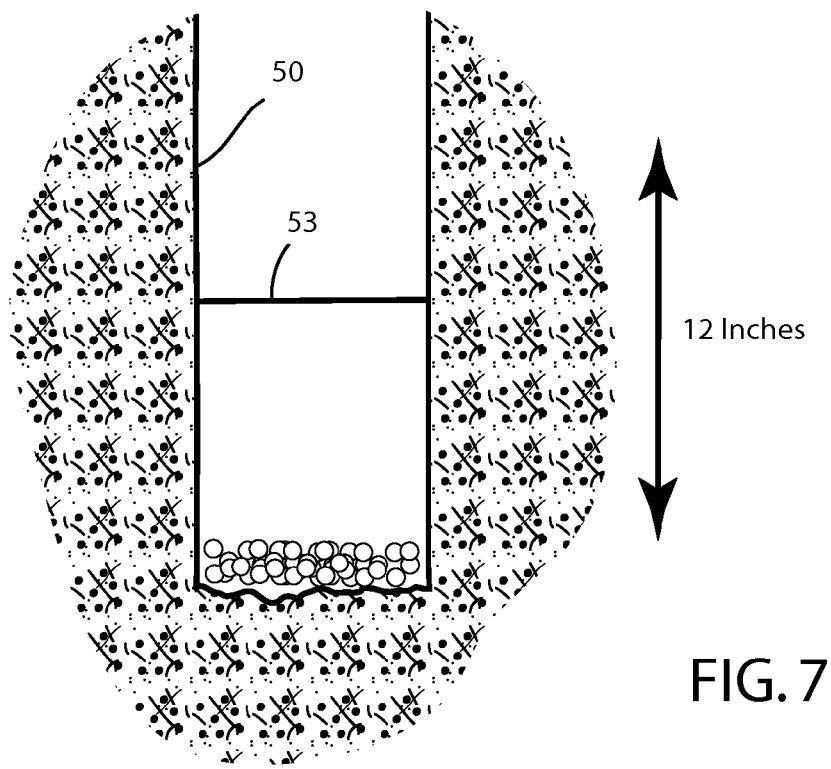
FIG. 7 is a side plan view of a test hole during perc testing.

FIG. 7 is a close-up of a side plan view of a test hole during perc testing, showing decreases in water level 53 as water soaks into the ground.

An example operation of the system is described below: An initial step of the present invention typically involves digging test holes. The test holes should typically be round and at least 6 inches, and generally 8 to 12 inches in diameter in most embodiments. However, other diameter holes are suitable in some implementations. The bottom of the percolation test hole should generally be at least 3 feet above the level of seasonally saturated soil or bedrock. A clam shell-type posthole digger can be used.

Next, the percolation test holes are prepared. The auger or posthole digger is likely to smear the soil along the sidewalls of the test hole. Therefore, the bottom 12 inches of the sidewalls and the bottom of the hole can be scratched or scarified with a sharp, pointed instrument such as a knife. Nails driven into a 1×2-inch board can be used for scarifying the hole to provide an open, natural soil into which water may percolate.

Once the hole has been dug, loose soil material is removed from the bottom of the test hole. Generally, 2 inches of one-fourth to three-fourths inch gravel can be added to protect the bottom from scouring when water is added. The gravel can be contained in a nylon mesh bag in order to be removed after the test is performed and used for additional percolation tests.

Next, the system of the invention is placed over the hole and is used to fill the percolation test hole with water to a depth of at least 12 inches above the soil bottom of the test hole. The percolation test may proceed immediately if the 12 inches of water seeps away in 10 minutes or less. This type of test is referred to as the "short test". For prolonged soil soaking, the system of the invention keeps the 12-inch level of water in the hole for at least four hours (for example), adding water as necessary. This period of time is referred to as the soaking period and is required as part of the "long test".

After the soaking period, the hole is to remain dry for 16 to 30 hours. This period of time is referred to as the swell period. The perc test measurement may begin following the swelling period. In certain embodiments the drop in the water level is measured to the nearest 1/16 inch approximately every 30 minutes. After each measurement, the water in the hole is refilled so that the liquid level is a preset distance above the gravel. The system continues taking measurements until three consecutive percolation rates vary by a range of no more than 10 percent.

In sandy soils, or other soils in which the first water seeps away in less than 30 minutes after the recommended swelling period, the system can adjust to allow a shorter period between measurements. The system continues taking readings until three consecutive percolation rates from one given hole, vary by no more than 10 percent.

Percolation rate is then calculated by dividing the time interval by the drop in water level to determine the percolation rate in minutes per inch (MPI). Examples: If the drop in water level is one inch in 30 minutes, the percolation rate is: 30 minutes/1 inch=30 mpi If the drop is 2½ inches in 10 minutes, then the percolation rate is: 10 minutes/2.5 inches=4 mpi.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

We claim:

1. A method of determining the percolation rate of soil, the method comprising:
    digging a hole into a soil area to be tested;
    providing a test assembly configured to be placed over the top of the hole, the test assembly containing a remote sensor positioned proximate the top of the hole;
    measuring the depth to the bottom of the hole using the remote sensor;
    automatically filling the hole to a specified level of water above the bottom of the hole, said filling determined by the remote sensor positioned proximate the top of the hole;
    maintaining the level of water in the hole by adding water to the hole when the water level is measured to be less than a specified level;
    maintaining the level of water in the hole for a predetermined period; and
    thereafter measuring decreases in the level of the water to determine percolation.

2. The method of claim 1, further comprising the step of making an initial determination as to whether the hole is retaining water above a certain rate of absorption.

3. The method of claim 1, further comprising a step of determining whether the hole has collapsed.

4. The method of claim 1, wherein the step of automatically filling the hole to a specified water level comprises filling the hole with a flexible hose extending from the test assembly to at least half way down the depth of the hole.

5. The method of claim 1, further comprising the step of determining the depth of the hole by adding water to create a substantially planar surface at the bottom of the hole.

6. The method of claim 1, further comprising recording the location of the remote sensor using an integrated global positioning system.

7. The method of claim 1, further comprising outputting the results to an integrated printer.

8. The method of claim 6, further comprising recording the position of the test using data from a global positioning system and outputting the results to an integrated printer.

9. The method of claim 1, further comprising communicating the results of the test using wireless functionality.

10. The method of claim 1, further comprising connecting multiple remote percolation test assemblies to conduct multiple tests simultaneously.

11. The method of claim 1, further comprising repeatedly testing an individual bore hole until three tests are conducted having a variation of measured perc rate of less than ten percent.

12. The method of claim 1, further comprising comparing the test results to area test results for consistency.

13. The method of claim 1, further comprising determining the addition or removal of unexpected water to identify erroneous tests.

14. The method of claim 1, further comprising use of a wireless link to communicate with the test assembly.

15. A percolation test apparatus comprising:
    a housing;
    a processor;
    a remote sensor configured to determine the depth of a hole from the top of the hole and to determine elevation of water in the hole from the top of the hole;
    a conduit configured to receive water from a source and allow passage of water from the water source to the hole; and
    a valve in communication with the processor configured to allow and inhibit water flow through the conduit; further comprising a wireless transmitter for communicating test results and/or location of the test to an external location.

16. The percolation test apparatus of claim 15, further comprising an integrated user interface.

17. The percolation test apparatus of claim 15, further comprising an integrated printer for outputting test results.

18. The percolation test apparatus of claim 15, further comprising a global positioning system receiver for determining location of a test.

19. The percolation test apparatus of claim 15, wherein the wireless transmitter is configured for wide area network communication and/or local area network communication.

20. The percolation test apparatus of claim 15, wherein a single housing contains a remote sensor, water control valve, processer, and battery.

21. The percolation test apparatus of claim 15, wherein the remote sensor is flush mounted or recessed into the base of a carrier case.

22. The percolation test apparatus of claim 15, wherein the percolation test apparatus comprises a dispensing hose configured to extend into a borehole.

* * * * *